(12) United States Patent
Velschow et al.

(10) Patent No.: US 10,743,804 B2
(45) Date of Patent: Aug. 18, 2020

(54) FLUID SAMPLING SYSTEM

(71) Applicant: Fluisense ApS, Allerød (DK)

(72) Inventors: Sten Velschow, Vedbæk (DK); Martin Toft Madsen, København Ø (DK)

(73) Assignee: Fluisense ApS, Allerød (DK)

( * ) Notice: Subject to any disclaimer, the term of this patent is extended or adjusted under 35 U.S.C. 154(b) by 274 days.

(21) Appl. No.: 14/423,939

(22) PCT Filed: Apr. 16, 2014

(86) PCT No.: PCT/DK2014/050102
§ 371 (c)(1),
(2) Date: Feb. 25, 2015

(87) PCT Pub. No.: WO2014/169924
PCT Pub. Date: Oct. 23, 2014

(65) Prior Publication Data
US 2016/0022191 A1    Jan. 28, 2016

(30) Foreign Application Priority Data

Apr. 17, 2013 (DK) .................................. 2013 70218

(51) Int. Cl.
*A61B 5/15* (2006.01)
*G01N 1/14* (2006.01)
(Continued)

(52) U.S. Cl.
CPC .... *A61B 5/150992* (2013.01); *A61B 5/15003* (2013.01); *A61B 5/155* (2013.01); *A61B 5/150229* (2013.01); *A61B 5/150755* (2013.01); *A61B 5/150946* (2013.01); *G01N 1/14* (2013.01); *G01N 1/28* (2013.01); *A61B 5/153* (2013.01); *A61B 5/150221* (2013.01); *A61B 5/150259* (2013.01)

(58) Field of Classification Search
None
See application file for complete search history.

(56) References Cited

U.S. PATENT DOCUMENTS

| 4,253,456 A | * | 3/1981 | Schindler | ............ | F04B 43/1215 |
| | | | | | 128/DIG. 13 |
| 4,633,878 A | * | 1/1987 | Bombardieri | ...... | A61B 5/14528 |
| | | | | | 600/347 |

(Continued)

FOREIGN PATENT DOCUMENTS

| EP | 0256415 A2 | 2/1988 |
| EP | 0389719 A2 | 10/1990 |

(Continued)

*Primary Examiner* — Sean P Dougherty
*Assistant Examiner* — Benjamin S Melhus
(74) *Attorney, Agent, or Firm* — Dinsmore & Shohl LLP

(57) ABSTRACT

A fluid sampling system comprising a housing, a first pump means for withdrawing at least one fluid sample from a first sample site, means for returning at least part of the at one fluid sample to a second sample site, transferring means for transferring at least one volume of the at least one first fluid to a sampling means, second pump means for providing at least one active substance, at least one connection to a reservoir containing the at least one active substance, and at least one energy source for driving at least the first and second pump means.

16 Claims, 1 Drawing Sheet

(51) Int. Cl.
  *G01N 1/28* (2006.01)
  *A61B 5/155* (2006.01)
  *A61B 5/153* (2006.01)

(56) References Cited

U.S. PATENT DOCUMENTS

| | | | |
|---|---|---|---|
| 6,017,318 | A | 1/2000 | Gauthier et al. |
| 6,451,610 | B1 | 9/2002 | Gorman et al. |
| 2006/0189926 | A1 | 8/2006 | Hall et al. |
| 2007/0239096 | A1* | 10/2007 | Keenan ............... A61B 5/14532 604/4.01 |
| 2008/0020794 | A1* | 1/2008 | Garon ................ A61B 5/14532 455/556.1 |
| 2008/0176271 | A1 | 7/2008 | Silver et al. |
| 2009/0221948 | A1* | 9/2009 | Szamosfalvi ....... A61M 1/3672 604/6.07 |
| 2009/0264720 | A1 | 10/2009 | Torjman et al. |
| 2011/0054276 | A1 | 3/2011 | Lowery |
| 2012/0022423 | A1* | 1/2012 | Sternby ................ A61K 31/191 604/6.07 |
| 2012/0123298 | A1 | 5/2012 | Mendels et al. |
| 2013/0060228 | A1* | 3/2013 | Pazart .............. A61B 5/150992 604/503 |
| 2014/0114211 | A1* | 4/2014 | Hadvary ........... A61M 5/14248 600/581 |
| 2014/0148749 | A1* | 5/2014 | Petisce ................ A61M 1/3621 604/5.01 |
| 2014/0163340 | A1* | 6/2014 | Say ...................... A61B 5/6866 600/309 |
| 2014/0235984 | A1* | 8/2014 | Wilbur ................ A61B 5/6866 600/365 |
| 2016/0270733 | A1* | 9/2016 | Hansson ............. A61B 5/0215 |

FOREIGN PATENT DOCUMENTS

| | | |
|---|---|---|
| JP | 2009527343 A | 7/2009 |
| WO | 9116416 A1 | 10/1991 |
| WO | 2008030927 A2 | 3/2008 |
| WO | 2012027312 A1 | 3/2012 |

* cited by examiner

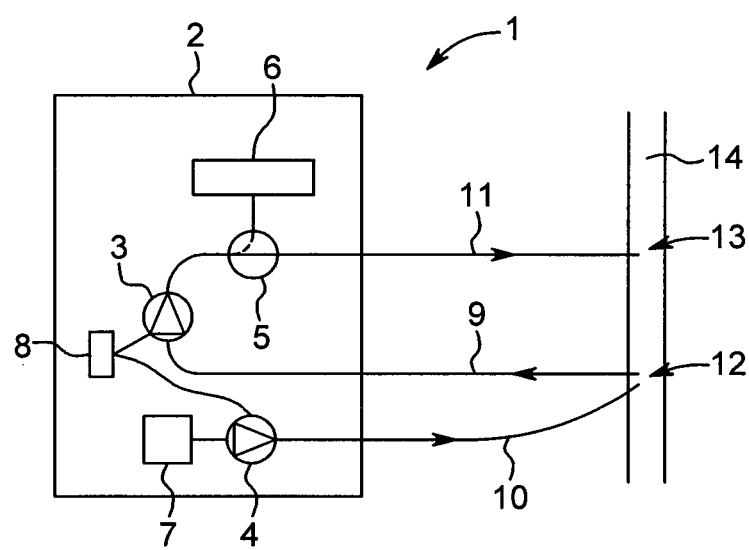

FLUID SAMPLING SYSTEM

CROSS REFERENCE TO RELATED APPLICATIONS

This application is the U.S. national phase of No. PCT/DK2014/050102, filed Apr. 16, 2014, which claims priority to Denmark application No. PA 2013 70218, filed Apr. 17, 2013, the contents of both of which are incorporated herein in their entirety.

FIELD OF INVENTION

The invention relates to a system for continuous and/or periodical fluid sampling

BACKGROUND OF THE INVENTION

In biomedical research monitoring processes in the living organism is a constant focus. Extracting blood or other body fluids from patients in order to diagnose disease states or monitor physiological conditions have applications in both intensive care hospital medicine, managing disease and interventions and in research.

Methods to monitor contents of analytes in blood generally involve accessing the circulation of the patient through a catheter venflon needle or other means.

The most common method is to extract a sample using a needle and vacuum tube whenever a blood parameter needs to be evaluated. For many blood constituents this approach is sufficient especially where the concentration of blood analytes are fairly stable and only infrequent samples need be taken.

For more labile blood constituents, such as glucose, metabolic markers, hormones and other signalling molecules such as adrenaline and cortisol the concentrations may change rapidly within a short time frame and may even be directly influenced by the sampling procedure itself.

If blood concentration of these constituents are to be frequently determined either frequent manual blood samples must be taken or an automatic sampling system used.

In a clinical setting where patients are hospitalised and fairly immobile in a bed a sampling system can be large and stationed on a desk or on a roller. If the system is to be used on outpatients, or under circumstances where connecting the patient to a larger device is not practical, for instance after trauma, in an ambulance, during transport inside or to and from a hospital a small portable system is needed.

SUMMARY OF THE INVENTION

Considering the issues described above, it is an aspect of the present invention to provide a system which enables continuous and/or periodic sampling of a fluid In a second aspect of the present invention is provided a system which is compact and portable.

These and other advantages are provided by a fluid sampling system comprising a housing, first pump means for withdrawing at least one fluid sample from a first sample site, means for returning at least part of the at least one fluid sample to a second sample site, transferring means for transferring at least one volume of the at least one first fluid to a sampling means, second pump means for providing at least one active substance at the first sample site, at least one connection to a reservoir containing the at least one active substance, and at least one energy source for driving at least the first and second pump means, and wherein fluid sampling system is adapted for withdrawing at least one fluid sample simultaneously as returning at least part of the at least one fluid sample.

Thus by the present invention is provided a fluid sampling system with means for obtaining one or more samples and for providing an active substance. The fluid sampling system enables that samples automatically are obtained continuously or periodically which means that no action by a user is required to initiate each withdrawal of a fluid sample.

The first pump means withdraws a fluid sample from a subject via e.g. at least a catheter connected to the first pump by for example a connector and tubing inside the fluid sampling system. Part of the withdrawn fluid I transferred to the sampling means and the remaining part of the withdrawn fluid may then be returned out of the fluid sampling device e.g. returned to the subject from whom the fluid sample was withdrawn. The fluid returned out of the fluid sampling system may preferably be forced out of the fluid sampling system through tubing/connectors/and or catheters by the incoming fluid withdrawn by the pumping action of the first pump means.

The first and second sample site may be the same or spaced apart. If the first and second sample site is the same or arranged within a small distance of each other only one incision needs to be made in the skin of the subject from which the fluid sample is to be taken.

If used to draw blood from a vein or artery; the first sample site is preferably positioned up stream in relation to the second sample site hereby minimising the risk of drawing blood that was returned at the second sample site.

It is to be understood that the second sample site is where at least part of the one fluid sample, can be returned. Thus, samples are not necessarily drawn from the second sample site and preferably no samples are drawn at the second sample site.

In situations where a subject e.g. a patient or an animal is to be monitored over a longer time interval the present invention may provide a great improvement to existing systems as the present invention both enables the automated sampling of a fluid as well as it enables the addition of an active substance.

The fluid sampling device may comprise automation means of various kinds allowing the fluid sampling system to be pre-programmed to e.g., obtain samples and/or provide an active substance continuously and/or at intervals. It is also possible that sampling may be randomized if this is advantageous as well as the fluid sampling system can be programmed to sample/provide active substance triggered by events such as physical activity of a test subject, time and/or results of test carried out on the sampled fluid etc.

Automation means may comprise storage means for programming of the fluid system, interact means such as buttons, diodes for signalling etc.

The housing is arranged to contain at least the main parts of the sampling system as described above. The housing can be shaped in order to be optimized for a specific purpose etc. and can be arranged to allow a light weight and/or compact system.

Preferably one or more surfaces of the housing is adapted to an ergonomic fit and/or to prevent that the housing causes discomfort and/or gets stuck in clothing etc.

The housing can be arranged with various means for fastening the system to e.g. a device or subject such as an animal or human from which one or more samples is to be obtained.

The first pump means is arranged to provide the pumping action needed to withdraw one or more samples from a first sample site. If the sample is a blood sample from a human or animal the sample is preferably obtained through a catheter. Inside the housing the transferring means transfers at least part of the sampled fluid to a sampling means and the remaining part of the sampled fluid is returned to the human or animal at a second sample site.

The first pump means is preferably a pump arranged to withdraw fluid in one or more pre-determined doses. Preferably the first pump means is a micro dosage pump arranged to withdraw small volumes of fluid. Preferably each withdrawn dose is 1 to 100 µl, 5 to 50 µl, up to 200 µl or even larger/smaller if desired. It is also possible the size of the withdrawn dose is varied automatically or e.g. by input from a user e.g. the volume of the withdrawn fluid sample (dose) is varied between e.g. 1 to 30 µl, 1 to 100 µl or even larger.

The first pump means may run continuously in which case fluid samples are withdrawn continuously. The first pump means may also run in intervals in which case samples are withdrawn in intervals. The intervals between withdrawal of fluid I.e. the intervals between the activation of the first pump means, can be predetermined, be automatically triggered by events such as physical activity or test results, and/or by interaction with a user i.e. by press of a button or a remote signal.

The second pump means provides at least one active substance at the first sample site. This can be done by arranging that the active substance is provided at a small distance from the first sample site the site, preferably, less than 1 mm.

The active substance can be of various types depending on e.g. what type of test is to be carried out on the sampled fluid. An active substance can also be added to e.g. a blood sample in order to prevent blood from clogging in a catheter, tubing inside the sampling system, test device and/or at or near the first or second sampling site.

The second pump means may provide the active substance or fluid containing the active substance at a flow rate of 0.01 µl-1 µl/s. or e.g. up to 2 µl or larger/smaller when needed.

The applicant has successfully shown that a system with a second pump providing an anti-coagulant at the first sample site at flow rate of 0.05 µl/s prevented clogging of the system over a time period of 24 hours and thus that blood still could be withdrawn from a first sample site after prolonged test time by use of the present invention.

The second pump means may preferably be arranged to provide a continuous and at least mainly constant flow of the one or more active substance. Thus the second pump means may provide the active substance even during periods where the first pump means is not running.

The active substance is preferably stored in a reservoir. The reservoir can be dimensioned to room a predetermined volume of active substance which is measured to be sufficient to a desired total time of sampling. The reservoir can be inside the fluid sampling system or outside. The reservoir can be a permanent part of the fluid sampling system or be exchangeable and/or removable. It is also possible that the reservoir can be refilled and thus the system and/or reservoir may be provided with means for refilling the reservoir.

The energy source of the fluid sampling system can be a battery which may be disposable or rechargeable. The energy source can be provided as one or more units such as one or more batteries. Also the energy source can be at least partly consisting of e.g. solar cells.

Preferably the energy source is small and/or light weight in order to enable a small and light weight fluid sampling system.

Preferably, the fluid sampling system is portable and/or the fluid sampling system is compact.

The fluid sampling system can comprise one or more catheters or be adapted to receive one or more catheters. The one or more catheters can be used to withdraw the fluid, return the fluid and provide the active substance.

The sampling means may be a Lab on a Chip (LoC), a means for fluid storage such as a container or a fabric as well as various other types of test or storage equipment in or outside the fluid sampling system.

The transferring means may include tubing, valves, motors, movable parts etc. which allows a preferably pre-determined volume of the samples fluid to be transferred to the sampling means. The transferring means may depend on the type of the sampling means.

Preferably at least one active substance is added at and/or near the first sample site as this may allow that the active substance is added volumetrically to the fluid which is sampled i.e. fluid and active substance is mixed and withdrawn together through the fluid sampling system. The active substance can be a fluid which is provided at the first sample site during sampling i.e. when a fluid sample is obtained as well as during periods where no fluid is withdrawn.

If the at least one active substance comprises an anti-coagulant the active substance may keep the fluid from coagulating if the fluid is blood.

Preferably the anticoagulant is rapidly metabolised when part of the fluid mixed with the active substance is returned to the subject in order to avoid any adverse effects on the subject.

For example the anticoagulant is [tri]sodiumcitrate e.g. where the solution of [tri]sodium citrate is hypertonic An active substance can also be a substance which is used as an internal reference for calibrating a sensor, as well as the active substance can be used as a reference for accurately determining a concentration of another substance.

A common challenge in portable analysis or diagnostic devices is how to calibrate sensors against known standards or when determining a concentration of an analyte to have a known concentration of a reference compound to enable accurate determination of an analyte in a sample. Without such calibration accurate quantitative determination of analytes is hard to obtain and in some cases impossible.

In some applications of the present invention where fluid samples are collected the sample is spiked with a predetermined concentration of a reference compound (an active substance) that can be measured in the quantitative analysis assay in a manner similar to that of the analyte for which the concentration needs to be determined.

For instance when analysing blood samples in biokinetic studies in pharmaceutical bioanalysis using HPLC or MS, it is common to add a reference compound with properties comparable to the sample analyte, and using the signal amplitude of the reference compound to get a quantitative determination of analytes rather than just a relative determination.

In the present invention this challenge is solved by adding a known concentration of reference compound to the second fluid i.e. the active substance which is volumetrically added to the sample at the time and site of sampling.

The internal standard added can be used to determine concentrations of analytes in the sample even if the sample is dried, diluted or otherwise altered.

In many embodiments the active substance is provided at a constant flow.

Preferably, the first and second pump means and any connected tubing, catheters, test devices are dimension in order to allow sampling of small volumes of fluid. Preferably the volumes of fluids withdrawn is 1-200 µl per dose or e.g. 30-600 µL fluid/minute in order to avoid adverse effect to the subject from which the sample is withdrawn.

The advantages of the fluid sampling system are enhanced if said system is compact allowing it to be mounted on a test subject during a longer period. A compact and light weight fluid sampling system can e.g. be carried by a patient e.g. a human under clothing enabling the patient to move around etc. It is also possible that the present invention can provide a fluid sampling system which is so compact and light weight that it enables it to be attached to a small animal such as a dog, cat, rat or even mouse. The present invention may also be attached to larger animals such as horses, pigs, cows and/or wild animals.

For example the fluid can be withdrawn through a first lumen, one or more active substance can be provided through a second lumen and/or the fluid can be returned through a third lumen where each of the first, second and third lumens are connected to the first and second pumps etc. inside the housing by at least one connector and various tubing. Preferably the first, second and/or third volume are parallel at least in the region at and/or near the first sample site which in this case is the same as the second sample site.

The fluid sampling system can be provided with the connected catheters/lumens or be provided arranged to be connected with catheters/lumens.

The fluid sampling system can be arranged to be used over a prolonged period. The prolonged period can be hours, 24 h, several days, weeks depending on the type of test carried out and the type of subject from which the sample is withdrawn.

Thus, the present invention is directed at enabling the process of repeatedly or continuously extracting very small volumes of blood or other bodily fluids automatically from a subject with minimal impact on the subject through catheters. Specifically we describe a system of pumps and fluids that enable construction of a miniaturised continuous sampling system which allows withdrawal of fluid over a prolonged period without the risk of clogging tubing, catheters, pumps or any test devices.

Ideally an automated blood sampling system is able to extract samples from a subject at any time point over the course of the day, unnoticed and without causing risk to the subject. The blood is by the present invention prevented from coagulating in the tubing, in the system itself and at the site of extraction and the coagulant properties of the subjects circulating blood should not be affected.

Further the compact design and optimized system means that the extracted amount of fluid can be so small as not to impact the subjects physiology even over extended periods of continuous sampling.

The smaller the diameter of the catheter the less discomfort to the subject and the present invention provides a system which may function even with diameters of minimal diameter.

Larger catheters need larger incisions in the skin to reach the vessels, resulting in larger wounds and more tissue damage.

A smaller catheter will affect a smaller volume of tissue and cause less inflammation.

DESCRIPTION OF THE DRAWINGS

The invention will in the following be described in greater detail with reference to the accompanying drawings:

FIG. 1 a schematic view of an embodiment according to the invention

DETAILED DESCRIPTION OF THE INVENTION

FIG. 1 shows an embodiment of a fluid sampling system 1 according to the invention having a housing 2 enclosing; a first pump 3, a second pump 4, transferring means 5 in the form of a valve, sampling means 6 and a reservoir 7 for an active substance and an energy source 8 in the form of a battery.

The battery 8 supplies energy to the second pump 4 which pumps an active substance, for example an anticoagulant fluid, from the reservoir 7 through a second lumen 10 to the first sampling site 12.

A sample is drawn through the first lumen 9 from the first sample site 12 to the valve 5 by means of the first pump 3. The battery 8 supplies energy to the first pump 3. The valve 5 can the direct the sample towards the sampling means 6 or back through the third lumen 11 to a second sampling site 13, preferably in the vicinity of the first sampling site 12.

The fluid sampling system 1 can be used to obtain continuous or periodical blood samples through the first lumen 9, from blood a vessel 14 in a body e.g. a human or an animal body, and into a sampling means 6 for testing and/or storing part of the blood and return the remaining blood to the blood vessel 14.

When drawing samples from a blood vessel 14 from an animal it is advantageous to be able to return unused blood to the animal as it will minimise the physiological effect which is caused by drawing blood.

An anticoagulant fluid or flushing fluid can be constantly infused at a flow rate of between 0.01 to 5 µl/s (microliters per second) in order to hinder clogging of the blood.

If no blood is sampled the infusion of anticoagulant fluid, e.g. Sodium Citrate based, is preferably done at a flow rate between 0.05 to 2 µl/s, preferably 0.1 µl/s in order to ensure that blood is kept from clogging in the system 1 and on the catheter or catheters inserted into the animal. It may also be preferable to circulate blood through the first lumen 9 and return it through the third lumen 11 in a relatively low flow rate between; 10 and 100 nl/s (nanoliter per second), preferably, 50 nl/s, in order to ensure that no clogging occurs in the system 1.

If blood is continually or periodically sampled the flow rate of the blood must be set so as to ensure that a suitable mixing ratio of blood and anticoagulant takes place. For citrate solutions (anticoagulant) this may e.g. be in the range of 1:8 to 1:15 depending on the citrate concentrations in the anticoagulant fluid. Preferably, the flow rate of the first fluid, when sampling, is between 0.1 and 5 µl/s, preferably 1 µl/s.

The invention claimed is:

1. A patient or animal fluid sampling system, comprising:
a housing;
a first pump operable to withdraw a fluid sample from a first sample site of a patient or animal;
a sampling lumen extending from the first sample site of the patient or animal to the first pump for withdrawing the fluid sample from the patient or animal, the first pump operable to transfer at least one volume of the fluid sample to a sampling device;
a return lumen extending from the first pump to a second sample site of the patient or animal for returning at least part of the fluid sample to the second sample site, the first pump operable to return at least part of the fluid sample through the return lumen, the second sample site being different than the first sample site;
a supply lumen for providing an active substance at and/or proximate the first sample site of the patient or animal;
a second pump, the supply lumen extending from the second pump to and/or proximate the first sample site and the second pump operable to provide the active substance through the supply lumen;
a connection to a reservoir containing the active substance, the active substance being an internal reference for calibrating a sensor or a reference for determining a concentration of another substance; and
at least one energy source operable to energize at least the first pump and second pump;
wherein the fluid sampling system is configured to allow mixing of the active substance provided at and/or proximate the first sample site with the fluid of the patient or animal, and further configured to withdraw the mixture of the fluid of the patient or animal and the active substance from the patient or animal at the first sample site.

2. A patient or animal fluid sampling system according to claim 1, wherein the active substance further comprises an anti-coagulant or a flushing fluid.

3. A patient or animal fluid sampling system according to claim 2, wherein the anti-coagulant is sodiumcitrate.

4. A patient or animal fluid sampling system according to claim 1, wherein the active substance is added proximate the first sample site.

5. A patient or animal fluid sampling system according to claim 1, wherein the reservoir of the active substance is arranged inside the housing.

6. A patient or animal fluid sampling system according to claim 1, wherein the reservoir is refillable.

7. A patient or animal fluid sampling system according to claim 1, further comprising one or more catheters for withdrawing the fluid sample, returning at least part of the fluid sample and/or providing the active substance.

8. A patient or animal fluid sampling system according to claim 1, wherein the active substance is used as the internal reference for calibrating a sensor.

9. A patient or animal fluid sampling system according to claim 1, wherein the active substance is used as a reference for accurately determining a concentration of another substance.

10. A patient or animal fluid sampling system according to claim 1, wherein the active substance is provided continuously.

11. A patient or animal fluid sampling system according to claim 1, wherein the first sample site is upstream with respect to the second sample site.

12. A method for sampling body fluid from a patient or animal comprising the steps of:
providing and extending a sampling lumen from a first sample site of the patient or animal to a first pump for withdrawing a fluid sample from the patient or animal;
withdrawing, continuously or periodically during time interval $\Delta t$, the fluid sample through the sampling lumen from the first sample site of the patient or animal;
automatically transferring at least part of the fluid sample to a sampling device for storage and/or analysis;
providing and extending a return lumen from the first pump to a second sample site of the patient or animal;
simultaneously returning to the patient or animal part of the sample fluid not transferred to the sampling device through the return lumen to the second sample site of the patient or animal, the second sample site being different than the first sample site and the sampling lumen being distinct from the return lumen;
providing and extending a supply lumen from a second pump to or proximate the first sample site of the patient or animal; and
providing an active substance through the supply lumen at or proximate the first sample site during time interval $\Delta t$, the active substance being an internal reference for calibrating a sensor or a reference for determining a concentration of another substance,
wherein the method for sampling body fluid is configured to allow mixing of the active substance provided at and/or proximate the first sample site with the fluid of the patient or animal, and further configured to withdraw the mixture of the fluid of the patient or animal and the active substance from the patient or animal at the first sample site.

13. A method for sampling body fluid from the patient or animal according to claim 12, comprising a step of providing the first sample site upstream with respect to the second sample site.

14. A method for sampling body fluid from the patient or animal according to claim 12, wherein the step of providing the active substance comprises providing the active substance continuously during the time interval $\Delta t$.

15. A method for sampling body fluid from the patient or animal according to claim 12, wherein the active substance further comprises an anti-coagulant or a flushing fluid.

16. A patient or animal fluid sampling system, comprising;
a housing;
a first pump operable to withdraw a fluid sample from a first sample site of the patient or animal;
a sampling lumen extending from the first sample site of the patient or animal to the first pump for withdrawing the fluid sample from the patient or animal;
a return lumen extending from the first pump to a second sample site of the patient or animal for returning at least part of the fluid sample to the second sample site, the first pump operable to return at least part of the fluid sample through the return lumen, the second sample site being different than the first sample site;
a valve directing the fluid sample withdrawn from the patient or animal by the first pump to a sampling device and to the second sample site, the first pump operable to return the fluid sample directed by the valve through the return lumen to the second sample site of the patient or animal or to the sampling device;
a supply lumen for providing an active substance at and/or proximate the first sample site of the patient or animal;
a second pump, the supply lumen extending from the second pump to and/or proximate the first sample site, the second pump being operable to provide the active substance through the supply lumen;
a connection to a reservoir containing the active substance, the active substance being an anti-coagulant, a flushing fluid, an internal reference for calibrating a sensor, or a reference for determining a concentration of another substance; and
at least one energy source operable to energize at least the first pump and second pump;
wherein the fluid sampling system is adapted for withdrawing the fluid sample simultaneously with returning the fluid sample to the patient or animal, and the fluid sampling system is configured to allow mixing of the active substance provided at and/or proximate the first sample site with the fluid of the patient or animal, and further configured to withdraw the mixture of the fluid of the patient or animal and the active substance from the patient or animal at the first sample site.

* * * * *